(12) United States Patent
Suzuki et al.

(10) Patent No.: US 11,428,926 B2
(45) Date of Patent: Aug. 30, 2022

(54) IMAGE PROJECTION DEVICE

(71) Applicant: QD LASER, INC., Kawasaki (JP)

(72) Inventors: Makoto Suzuki, Kawasaki (JP);
Megumi Yamamoto, Kawasaki (JP);
Seiji Morino, Kawasaki (JP); Chizuru Kaneko, Kawasaki (JP)

(73) Assignee: QD LASER, INC., Kawasaki (JP)

( * ) Notice: Subject to any disclaimer, the term of this patent is extended or adjusted under 35 U.S.C. 154(b) by 172 days.

(21) Appl. No.: 16/619,437

(22) PCT Filed: Sep. 12, 2018

(86) PCT No.: PCT/JP2018/033827
§ 371 (c)(1),
(2) Date: Dec. 4, 2019

(87) PCT Pub. No.: WO2019/065245
PCT Pub. Date: Apr. 4, 2019

(65) Prior Publication Data
US 2021/0173199 A1 Jun. 10, 2021

(30) Foreign Application Priority Data
Sep. 29, 2017 (JP) .............................. JP2017-189998

(51) Int. Cl.
*G02B 26/10* (2006.01)
*A61B 3/00* (2006.01)
(Continued)

(52) U.S. Cl.
CPC ............ *G02B 26/10* (2013.01); *A61B 3/0008* (2013.01); *A61B 3/024* (2013.01); *A61B 3/032* (2013.01);
(Continued)

(58) Field of Classification Search
CPC ....... A61B 3/024; A61B 3/0091; A61B 3/032; A61B 3/0033; A61B 3/0041;
(Continued)

(56) References Cited

U.S. PATENT DOCUMENTS

| 6,081,304 A | 6/2000 | Kuriyama |
| 6,227,667 B1 | 5/2001 | Halldorsson |

(Continued)

FOREIGN PATENT DOCUMENTS

| CN | 103140791 A | 6/2013 |
| CN | 103592762 A | 2/2014 |

(Continued)

OTHER PUBLICATIONS

Office Action of counterpart Chinese Patent Application No. 201880039696.5 dated Mar. 23, 2021 (10 sheets, 11 sheets translation, 21 sheets total).

(Continued)

*Primary Examiner* — William R Alexander
*Assistant Examiner* — Sharrief I Broome
(74) *Attorney, Agent, or Firm* — Kratz, Quintos & Hanson, LLP

(57) ABSTRACT

An image projection device includes: a light source that emits a laser beam; a control unit that generates an image light beam, and controls emission of the image light beam; a scan unit that scans the image light beam to convert it into scan light; a first light converging unit that is disposed before a user's eye, converges the scan light at a first convergence point near a pupil, and then irradiates the retina with the scan light to project the image on the retina; and a second light converging unit that converges the scan light at a second convergence point before the first light converging unit, and then irradiates the first light converging unit with the scan light; wherein a scan angle of the scan light is substantially (Continued)

the same size as a convergence angle at which the scan light converges to the first convergence point.

17 Claims, 11 Drawing Sheets

(51) Int. Cl.
    *A61B 3/024*     (2006.01)
    *A61B 3/032*     (2006.01)
    *G02B 27/42*     (2006.01)
    *H04N 9/31*     (2006.01)

(52) U.S. Cl.
    CPC ......... *G02B 27/4227* (2013.01); *H04N 9/317* (2013.01)

(58) Field of Classification Search
    CPC ......... A61B 3/0025; A61B 3/14; A61B 3/113; A61B 3/0083; A61B 3/028; A61B 3/022; A61B 3/12; A61B 3/145; A61B 5/163; A61B 3/0008; A61B 3/063; A61B 5/16; A61B 3/02; A61B 3/0285; A61B 3/066; G02B 6/10; G02B 27/4227; H04N 9/317
    See application file for complete search history.

(56) References Cited

U.S. PATENT DOCUMENTS

| | | | |
|---|---|---|---|
| 2001/0010598 A1* | 8/2001 | Aritake | G02B 27/0172 359/632 |
| 2005/0140644 A1 | 6/2005 | Mukawa | |
| 2005/0206985 A1 | 9/2005 | Togino | |
| 2006/0072215 A1 | 4/2006 | Nishi | |
| 2007/0109619 A1 | 5/2007 | Eberl | |
| 2008/0212195 A1 | 9/2008 | Yamamoto | |
| 2009/0316115 A1* | 12/2009 | Itoh | G02B 27/40 353/20 |
| 2013/0182302 A1 | 7/2013 | Shikii | |
| 2014/0049831 A1* | 2/2014 | Takeda | G02B 27/0172 359/630 |
| 2015/0009236 A1* | 1/2015 | Saito | G01S 5/163 345/656 |
| 2016/0033771 A1 | 2/2016 | Tremblay | |
| 2016/0103324 A1* | 4/2016 | Arakawa | G02B 27/0172 351/158 |
| 2017/0219826 A1* | 8/2017 | Haseltine | G02B 5/3083 |
| 2017/0347881 A1 | 12/2017 | Noda | |

FOREIGN PATENT DOCUMENTS

| | | |
|---|---|---|
| CN | 104280883 A | 1/2015 |
| CN | 105264423 A | 1/2016 |
| CN | 106170729 A | 11/2016 |
| CN | 107106009 A | 8/2017 |
| JP | 2001-290102 A | 10/2001 |
| JP | 2003-315726 A | 11/2003 |
| JP | 2003-315727 A | 11/2003 |
| JP | 2004-102204 A | 4/2004 |
| JP | 2008-046253 A | 2/2008 |
| JP | 2008-58777 A | 3/2008 |
| JP | 2009-258686 A | 11/2009 |
| JP | 2009-268778 A | 11/2009 |
| JP | 2015-015563 A | 1/2015 |
| JP | 2015-111231 A | 6/2015 |
| JP | 2017-49478 A | 3/2017 |
| WO | 2004/029693 A1 | 4/2004 |
| WO | 2016/103489 A1 | 6/2016 |

OTHER PUBLICATIONS

Written Opinion of the International Searching Authority for International Application No. PCT/JP2018/033827 dated Dec. 4, 2018 (7 sheets translation).

Extended European Search Report for corresponding European Patent Application No. 18861853.2 dated Oct. 29, 2020 (9 sheets).

International Search Report for International Application No. PCT/JP2018/033827 dated Dec. 4, 2018 (2 sheets, 2 sheets translation, 4 sheets total).

Written Opinion of the International Searching Authority for International Application No. PCT/JP2018/033827 dated Dec. 4, 2018 (5 sheets).

Office Action for corresponding Japanese Patent Application No. 2019-535961: Notification of Reasons for Refusal dated Oct. 29, 2019 (4 sheets, 4 sheets translation, 8 sheets total).

Office Action of corresponding Chinese Patent Application No. 201880039696.5 dated Oct. 20, 2021 (6 sheets, 11 sheets translation, 17 sheets total).

* cited by examiner

FIRST EMBODIMENT

FIRST COMPARATIVE EXAMPLE

IMAGE PROJECTION DEVICE

TECHNICAL FIELD

The present invention relates to an image projection device.

BACKGROUND ART

There have been known image projection devices such as head-mounted displays (HMDs) that directly project an image on a retina of a user by using a light beam emitted from a light source. In such image projection devices, a method referred to as Maxwellian view is used. In Maxwellian view, scan light forming an image is converged near a pupil, and the image is then projected onto the retina. There have been known image projection devices described in Patent Document 1 and Patent Document 2 as image projection devices that directly projects an image on the retina, for example.

PRIOR ART DOCUMENTS

Patent Document

Patent Document 1: Japanese Patent Application Publication No. 2009-258686; and
Patent Document 2: Japanese Patent Application Publication No. 2008-46253

SUMMARY OF THE INVENTION

Problem to be Solved by the Invention

There have been known image projection devices that reflect the scan light with a projection mirror arranged in front of a user's eye, converge the scan light near the pupil of the user's eye, and then irradiate the retina with the scan light. However, in such image projection devices, distortion occurs in an image to be projected, and there is therefore room for improvement in terms of projecting a good-quality image.

The present invention has been made in view of the above problem, and aims to project the good-quality image.

Means for Solving the Problem

The present invention is an image projection device that project an image onto a users retina, including: a light source that emits a laser beam; a control unit that generates an image light beam based on input image data, and controls emission of the image light beam from the light source; a scan unit that scans the image light beam emitted from the light source to convert the image light beam into scan light; a first light converging unit that is disposed in front of a user's eye, converges the scan light at a first convergence point in the vicinity of a pupil of the user's eye, and then irradiates the retina with the scan light to project the image on the retina and a second light converging unit that converges the scan light scanned by the scan unit at a second convergence point in front of the first light converging unit, and then irradiates the first light converging unit with the scan light; wherein in the image light beam, a ratio of an optical path length between the second light converging unit and the second convergence point to an optical path length between the scan unit and the second light converging unit is substantially the same size as a ratio of an optical path length between the second convergence point and the first light converging unit to an optical path length between the first light converging unit and the first convergence point.

In the above configuration, a scan angle of the scan light by the scan unit may be substantially the same size as a convergence angle at which the scan light converges to the first convergence point.

The present invention is an image projection device that project an image onto a user's retina, including: a light source that emits a laser beam; a control unit that generates an image light beam based on input image data, and controls emission of the image light beam from the light source; a scan unit that scans the image light beam emitted from the light source to convert the image light beam into scan light; a first light converging unit that is disposed in front of a user's eye, converges the scan light at a first convergence point in the vicinity of a pupil of the user's eye, and then irradiates the retina with the scan light to project the image on the retina; and a second light converging unit that converges the scan light scanned by the scan unit at a second convergence point in front of the first light converging unit, and then irradiates the first light converging unit with the scan light; wherein a scan angle of the scan light by the scan unit is substantially the same size as a convergence angle at which the scan light converges to the first convergence point.

In the above configuration, in the image light beam, a ratio of an optical path length between the second light converging unit and the second convergence point to an optical path length between the scan unit and the second light converging unit may be substantially the same size as a ratio of an optical path length between the second convergence point and the first light converging unit to an optical path length between the first light converging unit and the first convergence point.

In the above configuration, the first light converging unit and the second light converging unit may be mirrors that reflect the scan light, and in the image light beam, a bending angle at the first light converging unit may be substantially the same size as a bending angle at the second light converging unit.

In the above configuration, a focal length of the second light converging unit may be shorter than that of the first light converging unit.

In the above configuration, the image projection device may include a first optical member for making the image light beam enter the first light converging unit as diffusion light that is provided at the second convergence point.

In the above configuration, the first optical member may have an optical characteristic which converts the image light beam into convergence light, and the image light beam may be condensed in front of the first light converging unit by the first optical member, and then become the diffusion light to enter the first light converging unit.

In the above configuration, the image projection device may include a second optical member for making the image light beam enter the second light converging unit as the diffusion light.

In the above configuration, the second optical member may have an optical characteristic which converts the image light beam into the convergence light, and the image light beam may be condensed in front of the second light converging unit by the second optical member, and then become the diffusion light to enter the second light converging unit.

In the above configuration, the second optical member may be provided on an optical path of the image light beam between the light source and the scan unit, and make the image light beam enter the scan unit as the convergence light, and the image light beam may be emitted from the scan unit as the convergence light, be condensed in front of the second light converging unit, and then become the diffusion light to enter the second light converging unit, be emitted from the second light converging unit as the diffusion light, be condensed in front of the first light converging unit by the first optical member, and then become the diffusion light to enter the first light converging unit, and be emitted from the first light converging unit as substantially collimated light.

In the above configuration, the light source may be disposed at a position facing the scan unit, the second light converging unit may include a half mirror, and the half mirror may transmit the laser beam emitted from the light source.

The present invention is an image projection device that project an image onto a user's retina, including: a light source that emits a laser beam; a control unit that generates an image light beam based on input image data, and controls emission of the image light beam from the light source; a scan unit that scans the image light beam emitted from the light source to convert the image light beam into scan light; a first light converging unit that is disposed in front of a user's eye, converges the scan light at a first convergence point in the vicinity of a pupil of the user's eye, and then irradiates the retina with the scan light to project the image on the retina; and a second light converging unit that converges the scan light scanned by the scan unit at a second convergence point in front of the first light converging unit, and then irradiates the first light converging unit with the scan light; wherein each of the first light converging unit and the second light converging unit includes a glass material, a diffractive surface, and a curved surface mirror, and the scan light is refracted and diffracted at a position of the diffractive surface, and reflected by the curved mirror.

In the above configuration, the light source may emit a plurality of laser beams having different wavelengths, and astigmatism due to a refraction characteristic of the glass material in the first light converging unit or the second light converging unit may be corrected by a diffraction characteristic of the diffractive surface.

In the above configuration, the image projection device may include a third optical member for making the image light beam enter the first light converging unit as diffusion light that is provided at the second convergence point; wherein the third optical member has an optical characteristic which converts the image light beam into convergence light, and the image light beam is condensed in front of the first light converging unit by the third optical member, and then becomes the diffusion light to enter the first light converging unit.

In the above configuration, the third optical member may have a diffractive surface on a surface thereof.

In the above configuration, the image projection device may include a fourth optical member for making the image light beam enter the second light converging unit as the diffusion light; wherein the fourth optical member has an optical characteristic which converts the image light beam into the convergence light, and the image light beam is condensed in front of the second light converging unit by the fourth optical member, and then becomes the diffusion light to enter the second light converging unit.

In the above configuration, the fourth optical member may have a diffractive surface on a surface thereof.

In the above configuration, in the image light beam, a ratio of an optical path length between the second light converging unit and the second convergence point to an optical path length between the scan unit and the second light converging unit may be substantially the same size as a ratio of an optical path length between the second convergence point and the first light converging unit to an optical path length between the first light converging unit and the first convergence point.

The present invention is a retina scanning type visual field and visual acuity test apparatus including the above image projection device.

Effects of the Invention

The present invention can project a good-quality image.

EMBODIMENTS FOR CARRYING OUT THE INVENTION

The following is a description of embodiments of the present invention, with reference to the drawings.

First Embodiment

Figure 1:
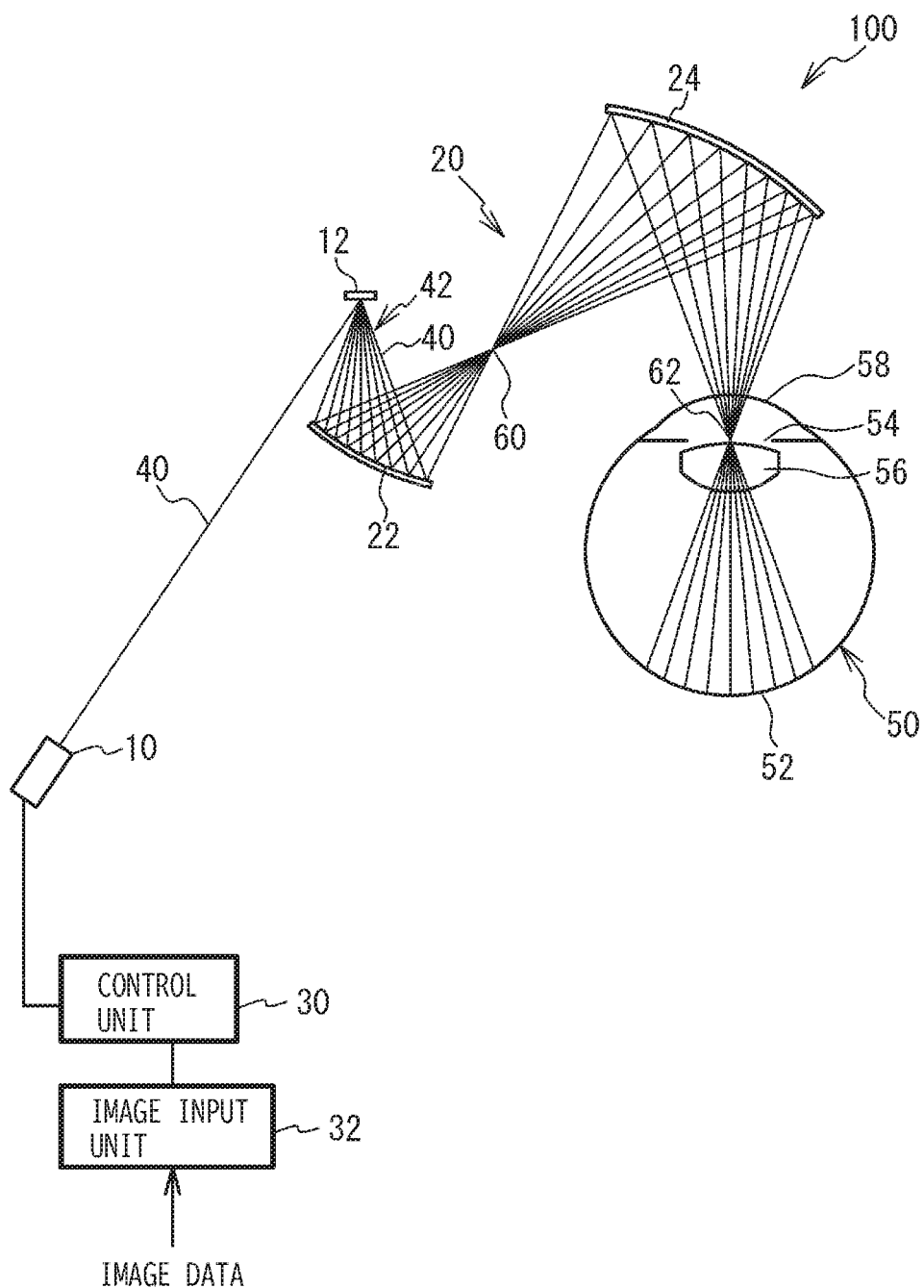
FIG. 1 is a view of an image projection device according to a first embodiment as viewed from above.
Figure 2:
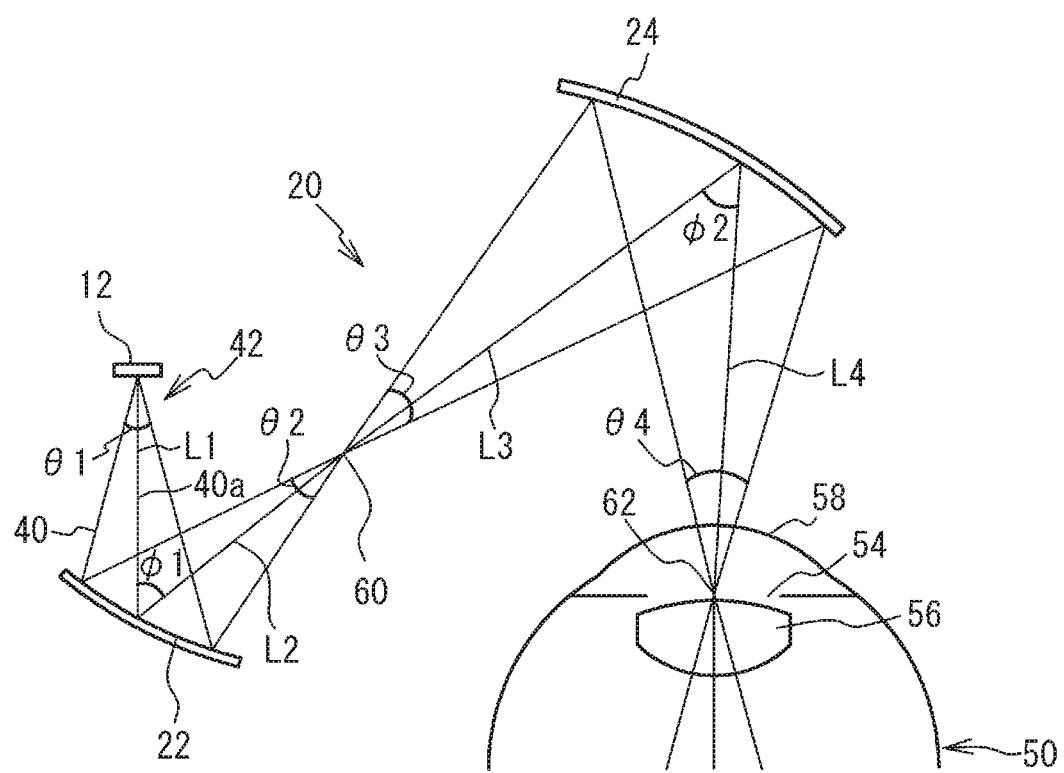
FIG. 2 is an enlarged view of a part related to a projection optical system of FIG. 1.

FIG. 1 is a view of an image projection device according to a first embodiment as viewed from above. FIG. 2 is an enlarged view of a part related to a projection optical system of FIG. 1. As illustrated in FIG. 1, an image projection device 100 of the first embodiment includes a light source 10, a scan mirror 12, a projection optical system 20, a control unit 30, and an image input unit 32. The image projection device 100 of the first embodiment is of an eyeglass type. A temple of an eyeglass is equipped with the light source 10, for example. A lens of the eyeglass is equipped with the scan mirror 12 and the projection optical system 20, for example. The control unit 30 and the image input unit 32 are not mounted on the eyeglass, but may be mounted on an external device (e.g. a mobile terminal) or on the temple of the eyeglass, for example.

Image data is input to the image input unit 32 from a camera and/or a recorder or the like (not shown). In accordance with the input image data, the control unit 30 controls emission of a laser beam 40 from the light source 10, and controls scanning of the scan mirror 12. Under the control of the control unit 34, the light source 10 emits a visible laser beam of, for example, a red laser beam (wavelength: about 610 nm to 660 nm), a green laser beam (wavelength: about 515 nm to 540 nm), and a blue laser beam (wavelength: about 440 nm to 480 nm). The light source 10 emitting the red, the green and the blue laser beams may be a light source formed by integrating laser diode chips of red, green, and blue (RGB) and a tricolor combining device, for example. The light source 10 is a single light source unit in which the laser diode chips and the tricolor combining device are integrated in a single module. Here, the light source 10 may emit the laser beam having a single wavelength. In this manner, the image data is converted into the laser beam 40, which is an image light beam, by the light source 10.

The control unit 30 is a processor such as a central processing unit (CPU), for example. When the camera 40 is directed along the line of sight of a user's eye 50 and is disposed at an appropriate position in the image projection device 100, a line-of-sight image captured by the camera can be projected onto a retina 52. Alternatively, an image input from a recorder or the like may be projected, or a camera image and an image from the recorder or the like may be superimposed on each other by the control unit 30 so that a so-called augmented reality (AR) image can be projected.

The scan mirror 12 two-dimensionally scans the laser beam 40 emitted from the light source 10 to convert it into a scan light 42. The scan mirror 12 is a micro electro mechanical system (MEMS) mirror, for example, and two-dimensionally scans the laser beam 40 in a horizontal direction and a vertical direction. The scan light 42 canned by the scan mirror 12 enters the projection optical system 20.

The projection optical system 20 converges the scan light 42 scanned by the scan mirror 12 in the vicinity of a pupil 54 of the user's eye 50, and then irradiates the retina 52 with the scan light 42 to project the image onto the retina 52. The user recognizes the image by an afterimage effect of the scan light 42 applied to the retina 52.

As shown in FIGS. 1 and 2, the projection optical system 20 includes a reflection mirror 22 and a projection mirror 24. Reflection surfaces of the reflection mirror 22 and the projection mirror 24 are curved surfaces such as free curved surfaces. The reflection mirror 22 and the projection mirror 24 are concave mirrors having different focal lengths. The focal length of the reflection mirror 22 is shorter than that of the projection mirror 24. That is, a curvature radius of the reflection mirror 22 is smaller than that of the projection mirror 24.

The scan light 42 scanned by the scan mirror 12 enters the reflection mirror 22. The scan light 42 is reflected by the reflection mirror 22, converges at a convergence point 60, and then is emitted to the projection mirror 24. Thus, the reflection mirror 22 is an example of a second light converging unit that converges the scan light 42 at the convergence point 60 in front of the projection mirror 24, and then irradiates the projection mirror 24 with the scan light 42. The scan light 42 emitted to the projection mirror 24 is reflected by the projection mirror 24, converges at a convergence point 62 in the vicinity of the pupil 54, and then is emitted to the retina 52. Thus, the projection mirror 24 is an example of a first light converging unit that converges the scan light 42 at the convergence point 62 in the vicinity of the pupil 54, and then irradiates the retina 52 with the scan light 42. The reflection mirror 22 and the projection mirror 24 have a positive light condensing power.

A scan angle $\theta 1$ of the scan light 42 by the scan mirror 12 is the same size as a convergence angle $\theta 4$ at which the scan light 42 converges at the convergence point 62. That is, in the scan light 42, the scan mirror 12 and the convergence point 62 are in a conjugate relationship with the same magnification. For example, the scan angle $\theta 1$ of the scan light 42 by the scan mirror 12 is the same size as a convergence angle $\theta 2$ at which the scan light 42 converges at the convergence point 60. In the scan light 42, the scan mirror 12 and the convergence point 60 are in the conjugate relationship with the same magnification through the reflection mirror 22. That is, the reflection mirror 22 converges the scan light 42 to the convergence point 60 at a convergence angle $\theta 2$ that is substantially the same size as the scan angle $\theta 1$ of the scan light 42 by the scan mirror 12. For example, an emission angle $\theta 3$ at which the scan light 42 emits from the convergence point 60 (emission angle $\theta 3$=convergence angle $\theta 2$) is the same size as the convergence angle $\theta 4$ at which the scan light 42 converges at the convergence point 62. In the scan light 42, the convergence point 60 and the convergence point 62 are in the conjugate relationship with the same magnification through the projection mirror 24. That is, the projection mirror 24 converges the scan light 42 to the convergence point 62 at the convergence angle $\theta 4$ that is substantially the same size as the emission angle $\theta 3$ of the scan light 42 emitted from the convergence point 60. Thus, in the scan light 42, the scan mirror 12 and the convergence point 62 are in the conjugate relationship with the same magnification through the reflection mirror 22 and the projection mirror 24.

Here, the scan angle $\theta 1$ and the convergence angle $\theta 4$ are not limited to the complete same size, but may be substantially the same size. This also applies to the convergence angle $\theta 2$ and the emission angle $\theta 3$. The "substantially the same" indicates that these angles are the same to the extent that they hardly affect the quality of the image projected on the retina 52.

A bending angle $\varphi 1$ at the reflection mirror 22 of a laser beam 40a corresponding to a center pixel of the image projected on the retina 52 is the same size as a bending angle $\varphi 2$ at the projection mirror 24 thereof. Also in the laser beam 40 other than the laser beam 40a, the bending angle at the reflection mirror 22 is the same size as the bending angle at the projection mirror. Here, the bending angle is the sum of an incident angle and a reflection angle.

Moreover, in the laser beam 40a, a ratio of an optical path length L2 between the reflection mirror 22 and the convergence point 60 to an optical path length L1 between the scan mirror 12 and the reflection mirror 22 is the same size as a ratio of an optical path length L3 between the convergence point 60 and the projection mirror 24 to an optical path length L4 between the projection mirror 24 and the convergence point 62. That is, a formula "(optical path length L2/optical path length L1)=(optical path length L3/optical path length L4)" is satisfied. Also in the laser beam 40 other than the laser beam 40a, the ratio of the optical path length between the reflection mirror 22 and the convergence point 60 to the optical path length between the scan mirror 12 and the reflection mirror 22 is the same size as the ratio of the optical path length between the convergence point 60 and the projection mirror 24 to the optical path length between the projection mirror 24 and the convergence point 62.

Here, the bending angle at the reflection mirror 22 and the bending angle at the projection mirror 24 of the laser beam 40 are not limited to the complete same size, but may be substantially the same size. Moreover, in the laser beam 40, the ratio of the optical path length between the reflection mirror 22 and the convergence point 60 to the optical path length between the scan mirror 12 and the reflection mirror 22, and the ratio of the optical path length between the convergence point 60 and the projection mirror 24 to the optical path length between the projection mirror 24 and the convergence point 62 are not limited to the complete same, but may be substantially the same. The "substantially the same" indicates that they are the same to the extent that they hardly affect the quality of the image projected on the retina 52.

Figure 3:
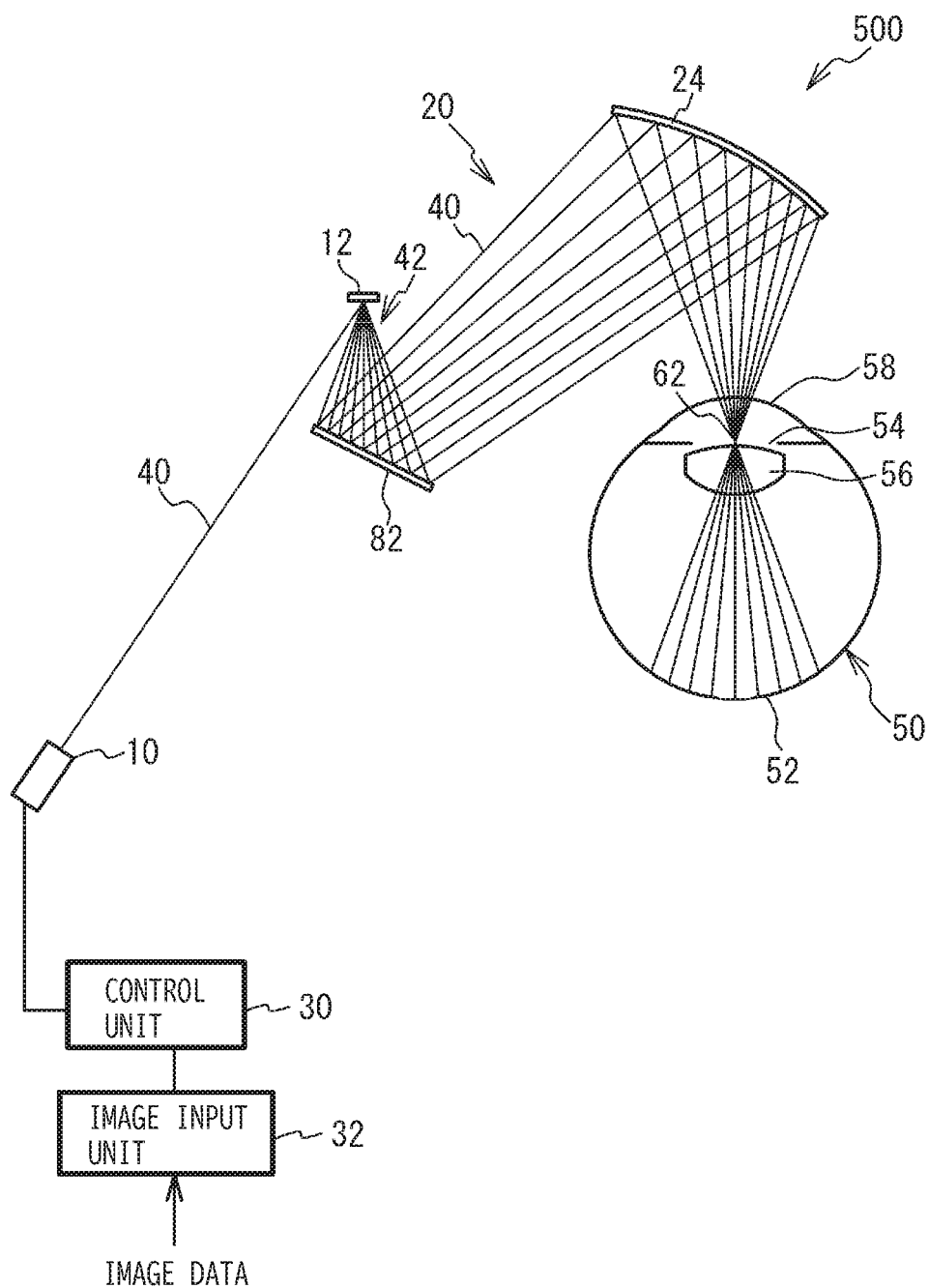
FIG. 3 is a view of an image projection device according to a first comparative example as viewed from above.

FIG. 3 is a view of an image projection device according to a first comparative example as viewed from above. As illustrated in FIG. 3, in an image projection device 500 of the first comparative example, the projection optical system 20 includes a reflection mirror 82 instead of the reflection mirror 22. The reflection mirror 82 is a planar mirror or a substantially planar mirror. Therefore, the scan light 42 is reflected by the reflection mirror 82, and it is then emitted to the projection mirror 24 with almost no convergence. Other structures are the same as those of the first embodiment, and the description thereof is thus omitted.

Figure 4A:
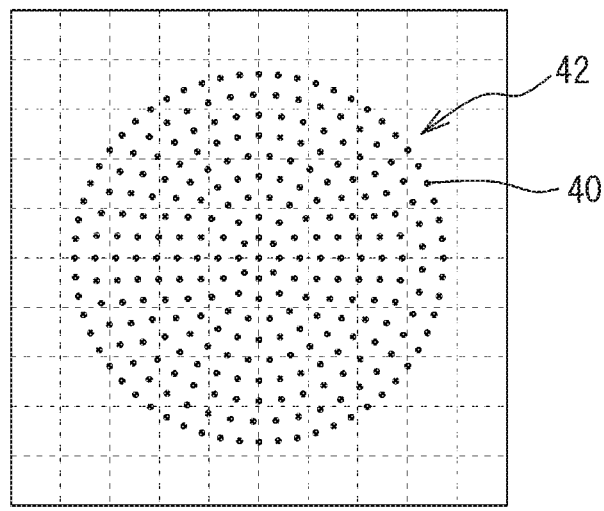
FIG. 4A and FIG. 4B are diagrams showing results of a simulation which has evaluated a laser beam with which a user's retina is irradiated.
Figure 4B:
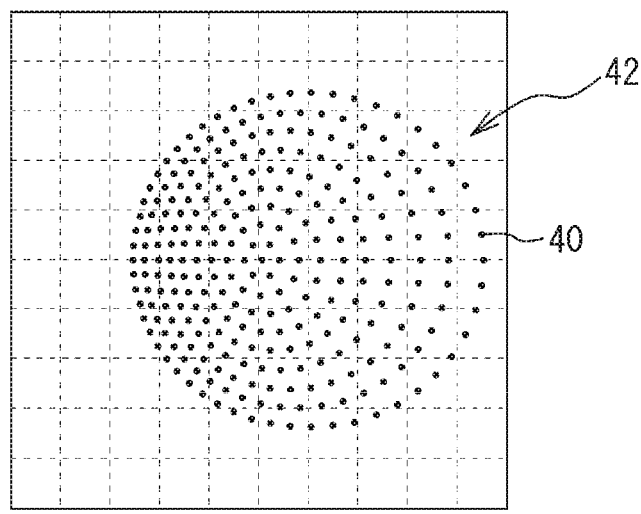

FIG. 4A and FIG. 4B are diagrams showing results of a simulation which has evaluated the laser beam with which the user's retina is irradiated. The simulation has evaluated how the scan light 42 with which the retina 52 is irradiated is changed when the scan light 42 scanned by the scan mirror 12 is circular and the laser beam 40 is evenly distributed. FIGS. 4A and 4B show the scan light 42 recognized by the user, a horizontal direction corresponds to a right-and-left direction of the user's eye 50, and a vertical direction corresponds to an up-and-down direction thereof.

The image projection device 500 of the first comparative example led the result that the scan light 42 was circular, but was shifted from the center of the eye 50 in the right-and-left direction, and the laser beam 40 was unevenly distributed, as shown in FIG. 4B. In this way, it is considered that the distribution of the laser beam became uneven because the projection mirror 24 having the positive light condensing power was used to converge the scan light 42 at the convergence point 62 in the vicinity of the pupil 54. When the distribution of the laser beam 40 is unevenly biased, the image recognized by the user becomes a distorted image.

On the other hand, the image projection device 100 according to the first embodiment led the result that the scan light 42 was circular and positioned at the center of the eye 50, and the laser beam 40 was evenly distributed as in when being scanned with the scan mirror 12, as shown in FIG. 4A. Thus, in the first embodiment, it is considered that the distribution of the laser beam 40 is kept evenly because of the following reason. That is, in the first embodiment, the reflection mirror 22 having the positive light condensing power is used in addition to the projection mirror 24 having the positive light condensing power. As described above, in the laser beam 40, the ratio of the optical path length between the reflection mirror 22 and the convergence point 60 to the optical path length between the scan mirror 12 and the reflection mirror 22 is the same size as the ratio of the optical path length between the convergence point 60 and the projection mirror 24 to the optical path length between the projection mirror 24 and the convergence point 62. Thereby, the optical path of the laser beam 40 from the scan mirror 12 to the convergence point 60 via the reflection mirror 22 and the optical path of the laser beam 40 from the convergence point 60 to the convergence point 62 via the projection mirror 24 may have similar shapes with different sizes, and can be configured to have point-symmetry with respect to the convergence point 60. Thereby, it is considered that the influence of the positive light condensing power of the projection mirror 24 on the laser beam 40 is canceled by the influence of the positive light condensing power of the reflection mirror 22 on the laser beam 40. Therefore, in the first embodiment, it is considered that the distribution of the laser beam 40 is kept evenly.

According to the first embodiment, the reflection mirror 22 that converges the scan light 42 at the convergence point 60 in front of the projection mirror 24 is provided in addition to the projection mirror 24 that converges the scan light 42 at the convergence point 62 in the vicinity of the pupil 54. In the laser beam 40, the ratio of the optical path length between the reflection mirror 22 and the convergence point 60 to the optical path length between the scan mirror 12 and the reflection mirror 22 is substantially the same size as the ratio of the optical path length between the convergence point 60 and the projection mirror 24 to the optical path length between the projection mirror 24 and the convergence point 62. Thereby, the influence of the positive light condensing power of the projection mirror 24 on the laser beam 40 can be canceled by the influence of the positive light condensing power of the reflecting mirror 22 on the laser beam 40, as described with reference to FIG. 4A. Therefore, it is possible to project the good-quality image in which distortions and the like are suppressed.

Moreover, in the first embodiment, the reflection mirror 22 is merely provided instead of the reflection mirror 82, as compared with the first comparative example. For this reason, it is possible to project the good-quality image while suppressing an increase in the number of components and an increase in the size of the image projection device.

Moreover, according to the first embodiment, in the laser beam 40, the bending angle at the reflection mirror 22 is substantially the same size as the bending angle at the projection mirror 24. Thereby, the influence of the positive light condensing power of the projection mirror 24 on the laser beam 40 can be effectively canceled by the influence of the positive light condensing power of the reflecting mirror 22 on the laser beam 40.

Moreover, when the retina 52 is irradiated with the scan light 42 using one projection mirror 24 having the positive light condensing power as in the image projecting device 500 of the first comparative example, it occurs that the diameter of the laser beam 40 when entering a cornea 58 of the eye 50 is smaller than the diameter of the laser beam 40 when scanned by the scan mirror 12. This is because although the scan angle of the scan mirror 12 is small, the scan light 42 enters the user's eye 50 with a large swing angle. When the diameter of the laser beam 40 when entering the cornea 58 is reduced, it is difficult to project a high resolution image on the retina 52. This will be described using an experiment conducted by the inventor. The experiment was conducted on a plurality of users having different visual acuities of 0.04, 0.5, 0.9, and 1.2, and was carried out by measuring how good each user was able to visually recognize an image projected onto the retina 52 (for example, the line-of-sight image of the user captured by a camera) while the diameter of the laser beam 40 when entering the cornea 58 was varied. The image projected onto the retina 52 is an image that has a horizontal viewing angle of 20 degrees, a screen aspect ratio of 16:9, and a valid vertical resolution of 720. For example, if the length of an eyeball is 24 mm, the size of the image projected onto the retina 52 is 5700 μm in the horizontal direction and 3200 μm in the vertical direction.

Figure 5:
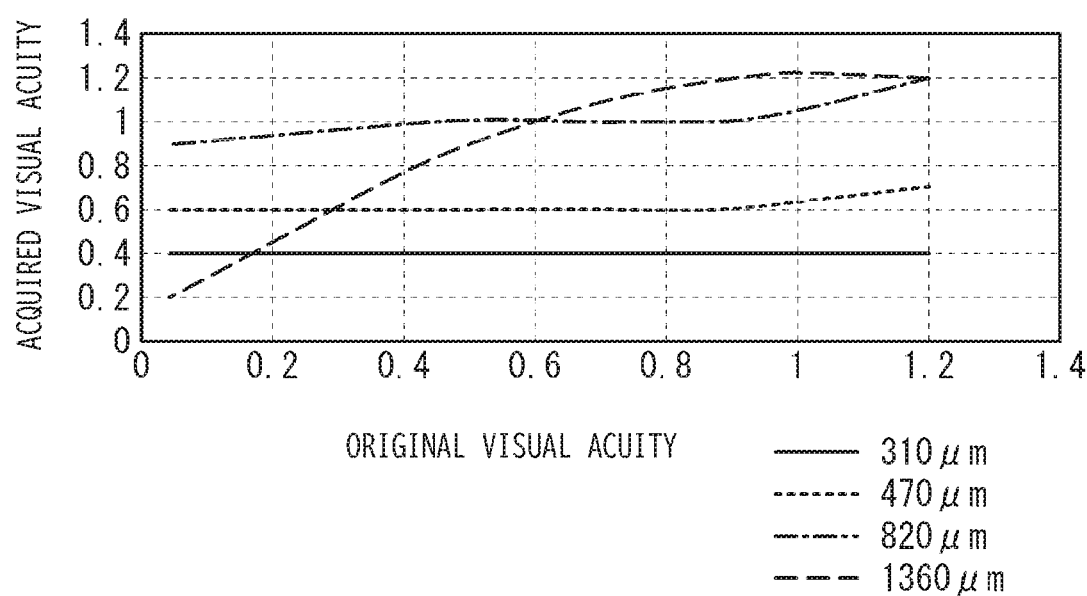
FIG. 5 is a diagram showing the results of an experiment conducted to examine a relationship between diameters of the laser beam and visual acuities when the laser beam enters the user's eye.

FIG. 5 is a diagram showing the results of an experiment conducted to examine a relationship between diameters of the laser beam and visual acuities when the laser beam enters the user's eye. In FIG. 5, a horizontal axis indicates an original visual acuity, and a vertical axis indicates an acquired visual acuity. The original visual acuity is a visual acuity measured by a conventional visual acuity test. The acquired visual acuity is a visual acuity for an image projected onto the retina 52 irradiated with the scan light 42. In FIG. 5, a solid line represents the result in the case where the diameter of the laser beam 40 when entering the cornea 58 was 310 μm, a dotted line represents the result in the case where the diameter was 470 μm, a dot-and-dash line represents the result in the case where the diameter was 820 μm, and a dashed line represents the result in the case where the diameter was 1360 μm. It should be noted that the laser beam 40 is entering the cornea 58 as substantially collimated light.

As shown in FIG. 5, in a case where the diameter of the laser beam 40 when entering the cornea 58 is as large as 820 μm or 1360 μm, the acquired visual acuity becomes high. That is, this reveals that the high-resolution image can be projected onto the retina 52 in the case where the diameter of the laser beam 40 when entering the cornea 58 is large, but it is difficult to project the high-resolution image on the retina 52 in the case where the diameter of the laser beam 40 when entering the cornea 58 is small.

Therefore, in the first embodiment, the scan angle θ1 of the scan light 42 by the scan mirror 12 and the convergence angle θ4 at which the scan light 42 converges at the convergence point 62 are made substantially the same in size, as shown in FIG. 2. That is, in the scan light 42, the scan mirror 12 and the convergence point 62 are in the conjugate relationship with the substantially same magnification. Thereby, the diameter of the laser beam 40 when entering the cornea 58 can be made substantially the same size as the diameter of the laser beam 40 when scanned by the scan mirror 12. Therefore, the high-resolution image can be projected.

Further, according to the first embodiment, the focal length of the reflection mirror 22 is shorter than the focal length of the projection mirror 24. Thereby, a gap between the reflective mirror 22 and the projection mirror 24 can be narrowed, and the image projection device can be made smaller in size. The reflection mirror 22 is preferably smaller than the projection mirror 24 from the viewpoint of downsizing of the image projection device.

As long as the reflection mirror 22 and the projection mirror 24 have the positive light condensing power, and optical characteristics for converging and then diffusing the light, they can also be configured by combining lenses and mirrors or using diffractive elements, except for the free curved surface mirrors.

Second Embodiment

Figure 6:
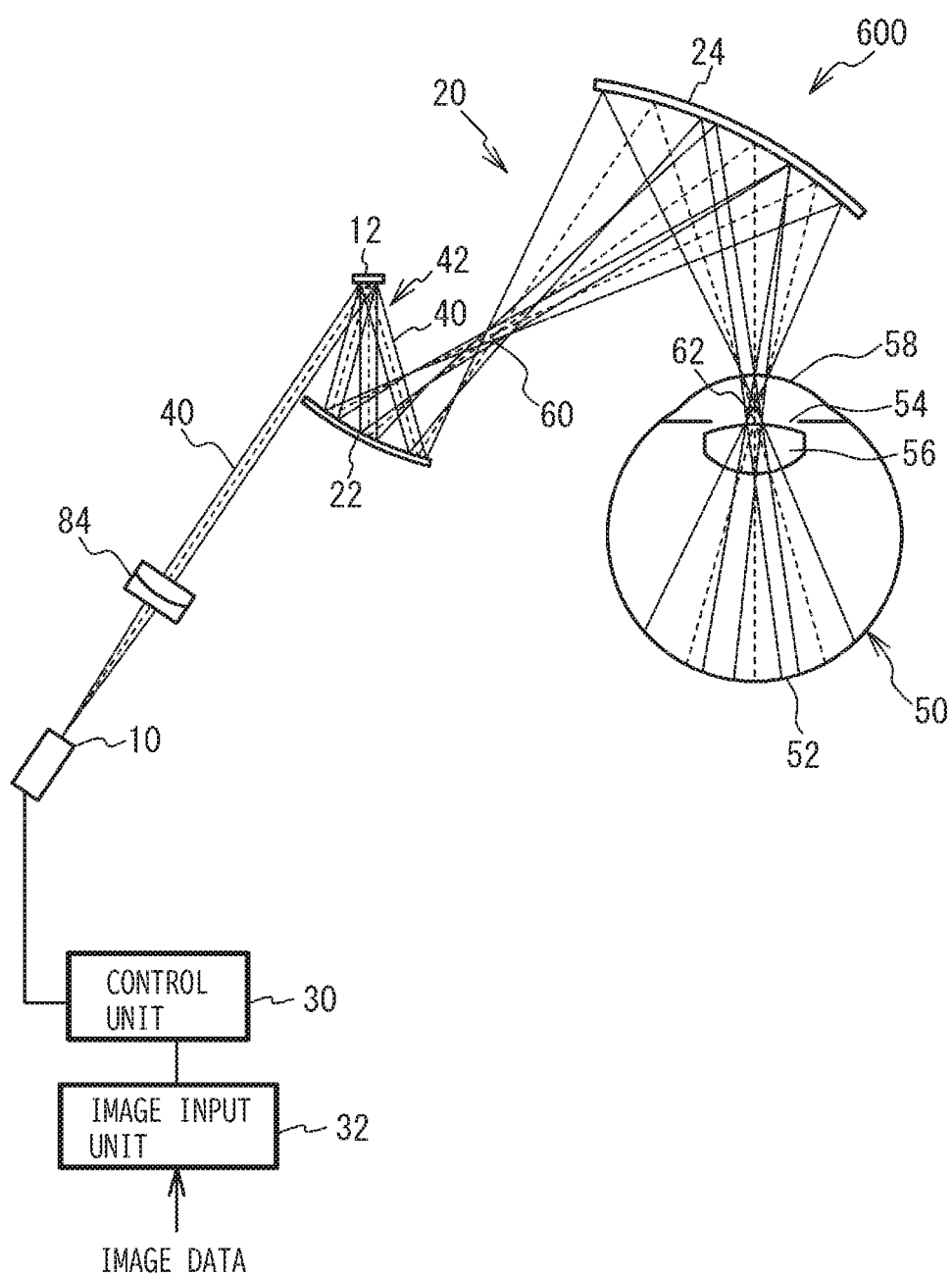
FIG. 6 is a view of an image projection device according to a second comparative example as viewed from above.

FIG. 6 is a view of an image projection device according to a second comparative example as viewed from above. Since the laser beam 40 has a diameter with a given size, it is shown in FIG. 6 as the laser beam 40 having a diameter Converging the scan light 42 scanned by the scan mirror 12 at one point is expressed as convergence, and focusing one laser beam 40 with the positive light condensing power is expressed as light condensing. As shown in FIG. 6, in an image projection device 600 of the second comparative example, a lens 84 is provided on the optical path of the laser beam 40 between the light source 10 and the scan mirror 12.

Other structures are the same as those of the image projection device 100 of the first embodiment, and the description thereof is thus omitted.

The laser beam 40, which is diffusion light emitted from the light source 10, is converted into the substantially collimated light by the lens 84 and enters the scan mirror 12. The laser beam 40 reflected by the scan mirror 12 enters the reflection mirror 22 as the substantially collimated light. Since the reflection mirror 22 has the positive light condensing power for converging the scan light 42 to the convergence point 60, when the laser beam 40 as the substantially collimated light enters the reflection mirror 22, the laser beam 40 reflected by the reflection mirror 22 is convergence light condensed in front of the convergence point 60. The laser beam 40 is condensed in front of the convergence point 60, and then becomes the diffusion light to enter the projection mirror 24. For this reason, the diameter of the laser beam 40 when entering the projection mirror 24 increases. Since the projection mirror 24 has the positive light condensing power for converging the scan light 42 to the convergence point 62 in the vicinity of the pupil 54, when the laser beam 40 having a large diameter enters the projection mirror 24, the laser beam 40 enters the eye 50 as the convergence light, is condensed in the vicinity of the pupil 54, and then becomes the diffusion light to enter the retina 52.

Thus, in the image projection device 600 of the second comparative example, the retina 52 is irradiated with the laser beam 40 as the diffusion light, so that the size of the laser beam 40 at the retina 52 is increased without being focused in the vicinity of the retina 52. For this reason, a defocus image is projected onto the retina 52.

Figure 7:
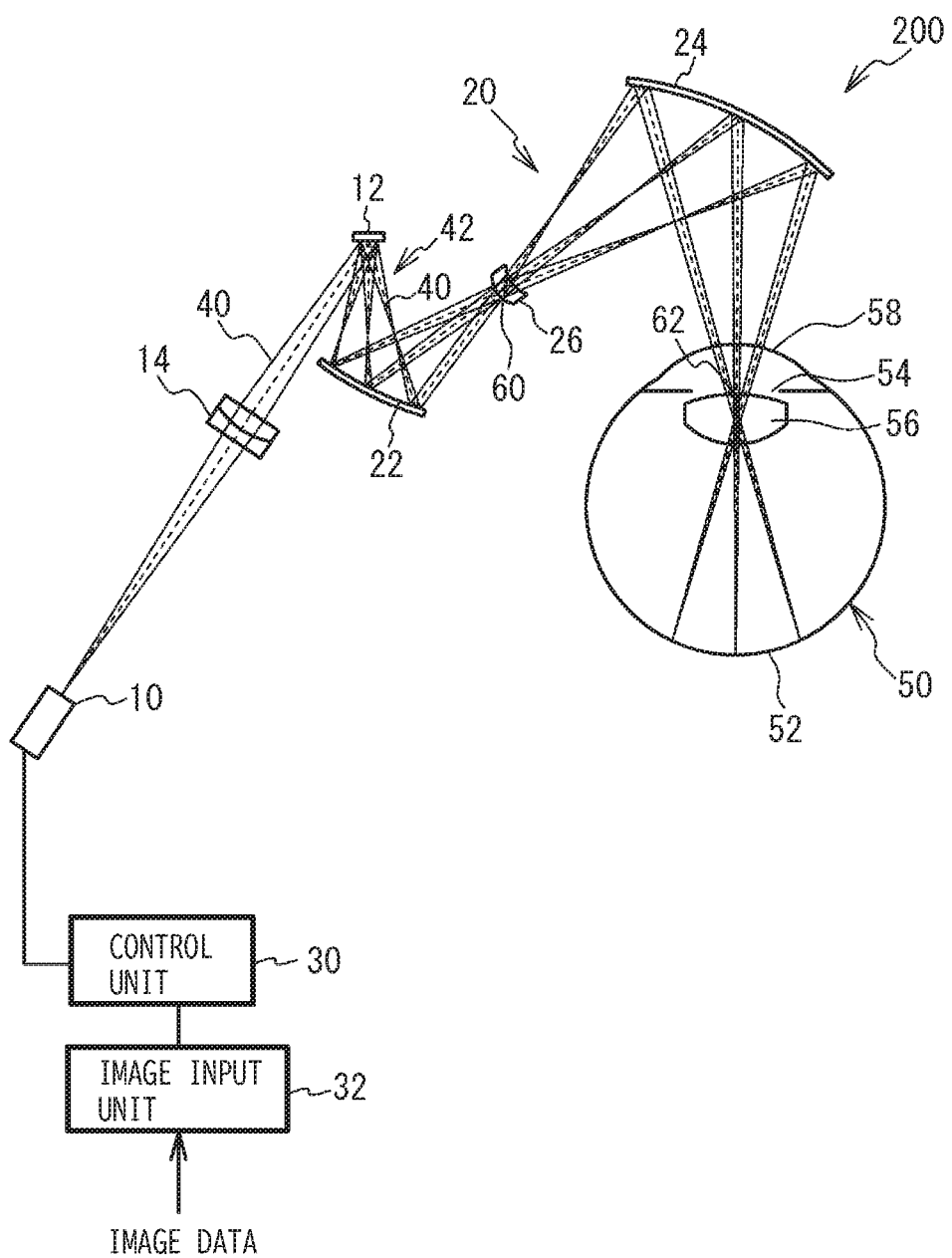
FIG. 7 is a view of an image projection device according to a second embodiment as viewed from above.

FIG. 7 is a view of an image projection device according to a second embodiment as viewed from above. Also in FIG. 7, the laser beam is shown as the laser beam 40 having the diameter as with FIG. 6. As shown in FIG. 7, in the image projection device 200 of the second embodiment, a lens 14 is provided on the optical path of the laser beam 40 between the light source 10 and the scan mirror 12. The projection optical system 20 includes a lens 26 at the convergence point 60 in addition to the reflection mirror 22 and the projection mirror 24. Other structures are the same as those of the image projection device 100 of the first embodiment, and the description thereof is thus omitted.

The lens 14 is a condensing lens that converts the laser beam 40, which is the diffusion light emitted from the light source 10, into the convergence light. Therefore, the laser beam 40 enters the scan mirror 12 as the convergence light. The laser beam 40 reflected by the scan mirror 12 remains as the convergence light, is condensed in front of the reflection mirror 22, and then becomes the diffusion light to enter the reflection mirror 22. Although the reflection mirror 22 has the positive light condensing power for converging the scan light 42 to the convergence point 60, the focal length of the lens 14 is set appropriately and a numerical aperture (NA) of the laser beam 40 when entering the reflection mirror 22 is set to an appropriate size. Thereby, the laser beam 40 reflected by the reflection mirror 22 becomes the diffusion light in which a diffusion level (a shape of spread of the diffusion light) is suppressed. The lens 26 is a condensing lens that converts the laser beam 40, which is the diffusion light in which the diffusion level is suppressed, into the convergence light. The laser beam 40 converted into the convergence light by the lens 26 is condensed in front of the projection mirror 24, and then becomes the diffusion light to enter the projection mirror 24. Since the projection mirror 24 has the positive light condensing power for converging the scan light 42 to the convergence point 62 in the vicinity of the pupil 54, the focal length of the lens 26 is set appropriately and the NA of the laser beam 40 when entering the projection mirror 24 is set to the appropriate size, whereby the laser beam 40 reflected by the projection mirror 24 becomes the substantially collimated light. The laser beam 40 enters the eye 50 as the substantially collimated light, and is focused in the vicinity of the retina 52 by a crystalline lens 56.

Figure 8A:
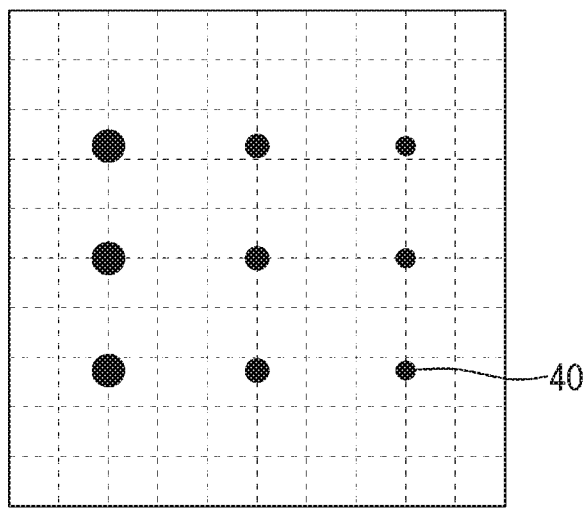
FIG. 8A and FIG. 8B are the results of a simulation which evaluated the laser beam with which the user's retina was irradiated when a focal length of a lens provided at a convergence point of a reflection mirror was varied.
Figure 8B:
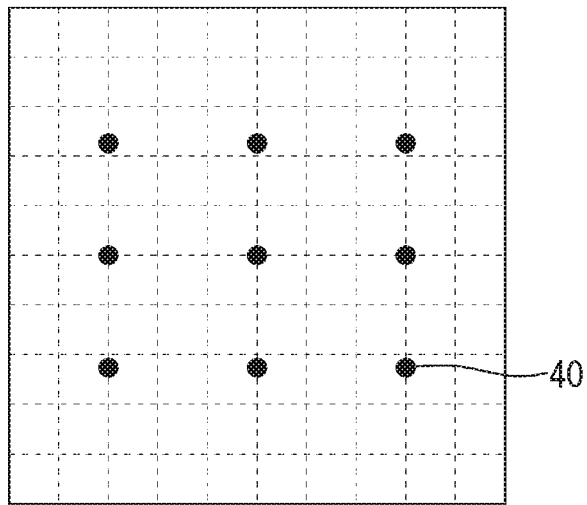

FIG. 8A and FIG. 8B are the results of a simulation which evaluated the laser beam with which a plane virtually provided at the position of the user's retina was irradiated when the focal length of the lens provided at the convergence point of the reflection mirror was varied. FIGS. 8A and 8B represent the laser beam 40 recognized by the user, a horizontal direction corresponds to the right-and-left direction of the user's eye 50, and a vertical direction corresponds to the up-and-down direction thereof. FIG. 8A shows a result of the simulation when the focal length of the lens 26 is not appropriate, and FIG. 8B shows a result of the simulation when the focal length of the lens 26 is appropriate. When the focal length of the lens 26 is not appropriate, it occurs that the diameters of the laser beam 40 projected on the plane virtually provided at the position of the retina 52 are different in the right-and-left direction of the eye 50 as shown in FIG. 8A. On the other hand, when the focal length of the lens 26 is appropriate, the diameters of the laser beam 40 are even in the up-and-down direction and the right-and-left direction of the eye 50 as shown in FIG. 8B.

According to the second embodiment, the lens 26 for making the laser beam enter the projection mirror 24 as the diffusion light is provided at the convergence point 60 of the scan light 42 reflected by the reflection mirror 22 as shown in FIG. 7. The laser beam 40 is made to enter the projection mirror 24 as the diffusion light, so that the laser beam 40 can be converted into the substantially collimated light by the positive light condensing power of the projection mirror 24, and the eye 50 can be irradiated with the substantially collimated light. Thereby, the laser beam 40 is focused on the vicinity of the retina 52 by the crystalline lens 56, so that the good-quality image in which defocusing is suppressed can be projected. Further, the lens 26 is provided at the convergence point 60, so that it can be easily realized that the plurality of laser beams 40 constituting the scan light 42 enter the projection mirror 24 as the appropriate diffusion light.

Further, according to the second embodiment, the lens 26 has an optical characteristic which converts the laser beam 40 into the convergence light, and the laser beam 40 is condensed in front of the projection minor 24 by the lens 26 and then becomes the diffusion light to enter the projection mirror 24, as shown in FIG. 7. Thereby, the NA of the laser beam 40 when entering the projection minor 24 can be adjusted well, so that it can be satisfactorily achieved that the laser beam 40 reflected by the projection minor 24 becomes the substantially collimated light.

Further, according to the second embodiment, the lens 14 for making the laser beam 40 enter the reflection mirror 22 as the diffusion light is provided as shown in FIG. 7. Thereby, the laser beam 40 in which the diffusion level is suppressed by the positive light condensing power of the reflection mirror 22 can be made to enter the lens 26. Therefore, a lens having a special specification need not to be used as the lens 26 which makes the laser beam 40 enter the projection mirror 24 as the appropriate diffusion light.

Further, according to the second embodiment, the lens 14 has an optical characteristic which converts the laser beam 40 into the convergence light, and the laser beam 40 is condensed in front of the reflection mirror 22 by the lens 14 and then becomes the diffusion light to enter the reflection mirror 22, as shown in FIG. 7. This facilitates adjustment of the diffusion level of the laser beam 40 when entering the lens 26.

As in the second embodiment, in order to provide both the good-quality image to the user and the downsizing of the image projection device, the laser beam 40 is emitted from the scan mirror 12 as the convergence light, is condensed in front of the reflection mirror 22, and then becomes the diffusion light to enter the reflection mirror 22. Then, it is preferable that the laser beam 40 is emitted from the reflection mirror 22 as the diffusion light, is condensed in front of the projection mirror 24 by the lens 26, and then becomes the diffusion light to enter the projection mirror 24, and is emitted from projection mirror 24 as the substantially collimated light.

Further, in the second embodiment, only the lens 26 is increased as compared with the second comparative example. Therefore, it is possible to project the good-quality image while suppressing an increase in the number of components and an increase in the size of the image projection device.

Here, in the second embodiment, the lens 26 may have a function suppressing chromatic aberration. Further, the lens 26 is preferably designed to suppress field curvature. The case where the lens 26 is an optical member for making the laser beam 40 enter the projection mirror 24 as the diffusion light has been described as an example. The case where the lens 14 is an optical member for making the laser beam 40 enter the reflection mirror 22 as the diffusion light has been described as an example. However, the optical member are not limited to the lens, may be the mirror or the diffractive element, and preferably has the optical characteristic that converts the laser beam 40 into the convergence light.

In the first and second embodiments, the reflection mirror 22 and the projection mirror 24 may include the diffractive element. The reflection mirror 22 is preferably a total reflection mirror that does not transmit the light. The projection mirror 24 may be a half mirror that can transmit the light in the line-of-sight direction of the user's eye 50, or may be the total reflection mirror that does not transmit the light. When the projection mirror 24 is the half mirror, an actual image in the line-of-sight direction can be transmitted and viewed together with the image by the laser beam 40. When the projection mirror 24 is the total reflection mirror, only the image by the laser beam 40 can be viewed.

Figure 9:
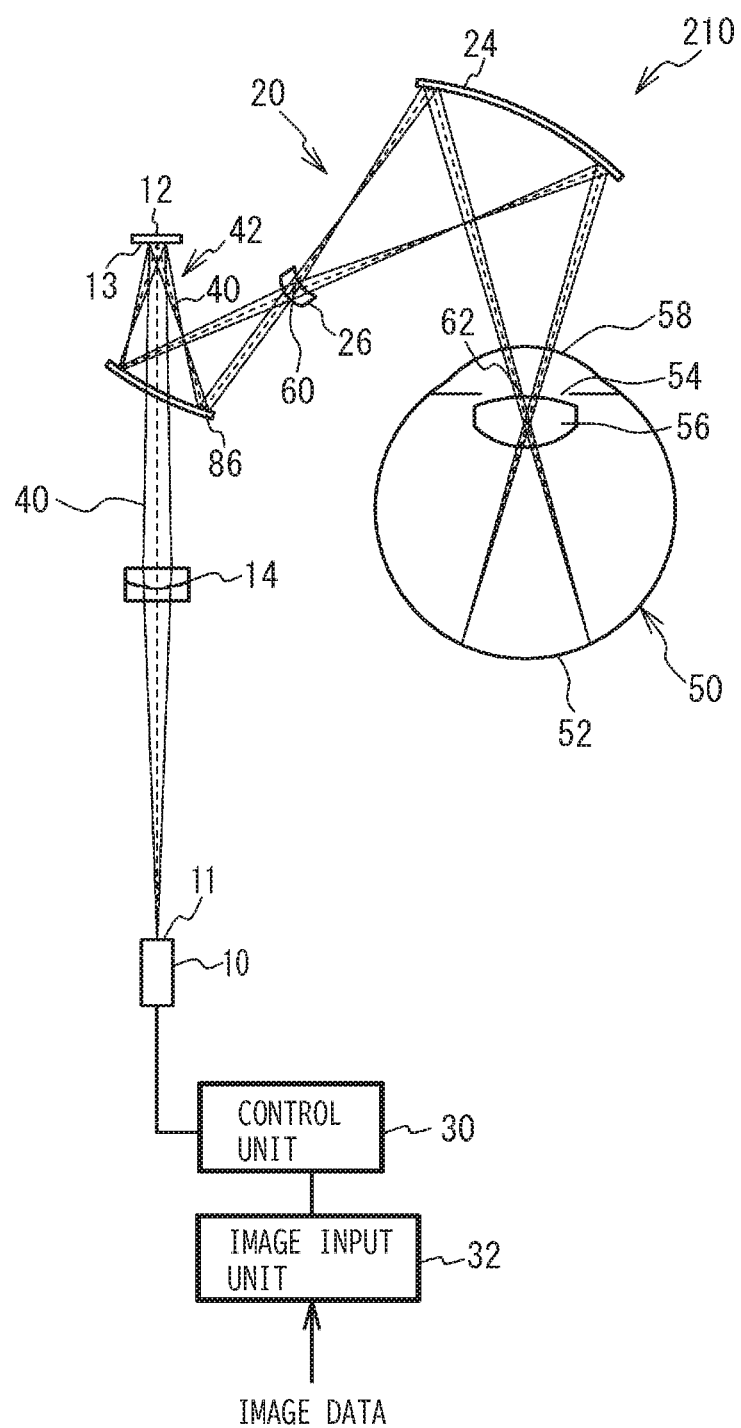
FIG. 9 is a view of an image projection device according to a first variation of the second embodiment as viewed from above.

FIG. 9 is a view of an image projection device according to a first variation of the second embodiment as viewed from above. As shown in FIG. 9, in an image projection device 210 according to the first variation of the second embodiment, the light source 10 and the lens 14 are arranged at positions facing the scan mirror 12. That is, an emission surface 11 of the light source 10 that emits the laser beam 40 faces a scan surface 13 of the scan mirror 12. Therefore, the laser beam 40 enters the scan surface 13 of the scan mirror 12 from a front thereof. When the light source 10 and the scan mirror 12 are arranged in such a positional relationship and the reflection mirror 22 is used as shown in the second embodiment, the laser beam 40 emitted from the light source 10 is blocked by the reflection mirror 22 and does not enter the scan mirror 12. Therefore, in the first variation of the second embodiment, a reflection half mirror 86 is used instead of the reflection mirror 22. The reflection half mirror 86 is a half mirror that transmits the laser beam 40 from the light source 10 side but reflects the reflection light from the scan mirror 12. Accordingly, the laser beam 40 emitted from the light source 10 transmits the reflection half mirror 86 and enters the scan mirror 12. The laser beam 40 reflected by the scan mirror 12 is reflected by the reflection half mirror 86. Other structures are the same as those of the image projection device 200 of the second embodiment, and the description thereof is thus omitted.

When the laser beam 40 obliquely enters the scan mirror 12 and is reflected as in the second embodiment, a projection image may be distorted in a horizontal trapezoid, and thus distortion may occur in the image projected on the retina 52. However, according to the first variation of the second embodiment, the light source 10 is disposed at a position facing the scan mirror 12. For this reason, the laser beam 40 enters the scan mirror 12 from the front thereof, and the distortion of the projection image to the horizontal trapezoid is reduced. As a result, the distortion of the image projected on the retina 52 is reduced.

Third Embodiment

Figure 10:
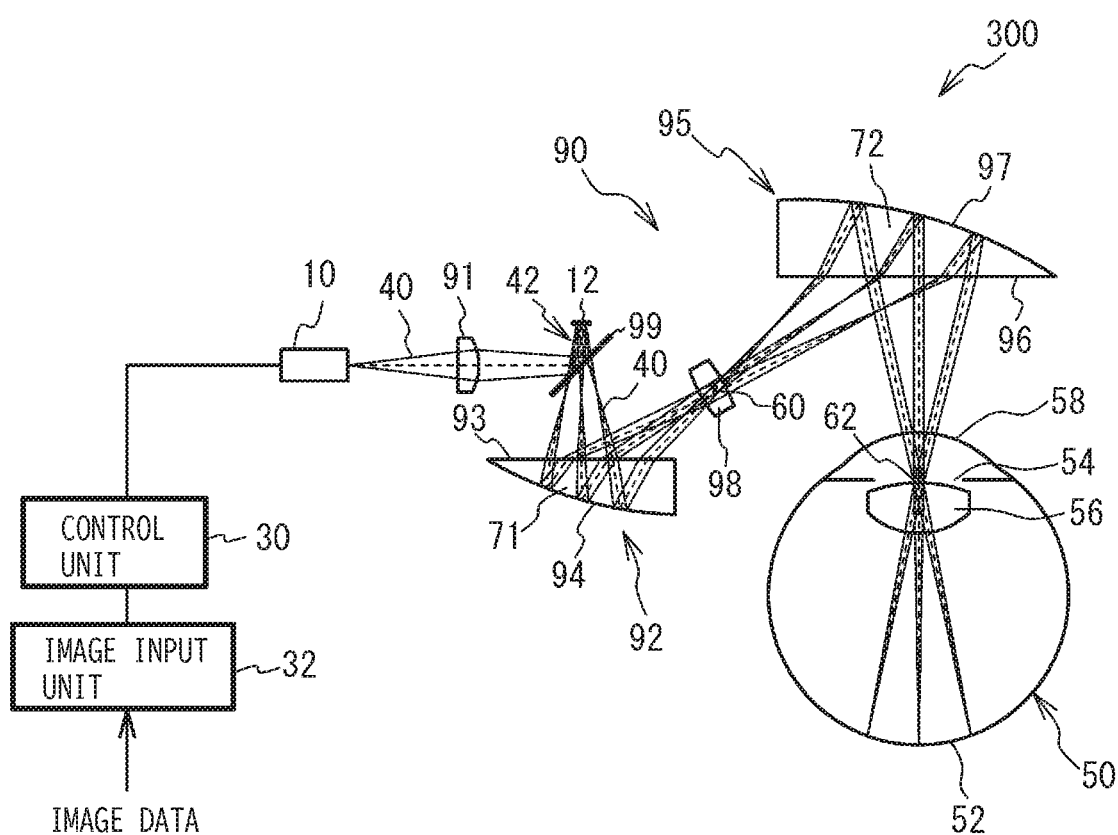
FIG. 10 is a view of an image projection device according to a third embodiment as viewed from above.

FIG. 10 is a view of an image projection device according to a third embodiment as viewed from above. As shown in FIG. 10, an image projection device 300 according to the third embodiment includes a projection optical system 90 instead of the projection optical system 20 according to the first embodiment. A lens 91 and a half mirror 99 are provided on the optical path of the laser beam 40 between the light source 10 and the scan mirror 12. The laser beam 40 emitted from the light source 10 passes through the lens 91, and then is reflected by the half mirror 99 to enter the scan mirror 12. The scan light 42 scanned by the scan mirror 12 transmits the half mirror 99. The projection optical system 90 includes a reflection unit 92 and a projection unit 95, and a lens 98 disposed at the convergence point 60 therebetween. Other structures are the same as those of the image projection device 100 of the first embodiment, and the description thereof is thus omitted.

The reflection unit 92 includes a glass material (lens) 71, a diffractive surface 93 that is a transmission type diffraction element located on an incident side of the scan light 42 in the glass material 71, and a free curved surface mirror 94 that is located opposite to the diffractive surface 93. The scan light 42 which has entered the reflection unit 92 is refracted and diffracted at the position of the diffractive surface 93, and transmits the glass material 71 in a direction of the free curved surface mirror 94. The free curved surface mirror 94 is a reflection mirror that has the positive light condensing power and reflects the scan light 42 which has transmitted the diffractive surface 93 and the glass material 71. As an example, the free curved surface mirror 94 is formed by depositing a reflection material on the glass material 71.

The projection unit 95 includes a glass material (lens) 72, a diffractive surface 96 that is a transmission type diffraction element located on an incident side of the scan light 42 in the glass material 72, and a free curved surface mirror 97 that is located opposite to the diffractive surface 96. The scan light 42 which has entered the projection unit 95 is refracted and diffracted at the position of the diffractive surface 96, and transmits the glass material 72 in a direction of the free curved surface mirror 97. The free curved surface mirror 97 is a reflection mirror that has the positive light condensing power and reflects the scan light 42 which has transmitted the diffractive surface 96 and the glass material 72. As an example, the free curved surface mirror 97 is formed by depositing a reflection material on the glass material 72.

At the positions of the diffractive surfaces 93 and 96, the scan light 42 is refracted by the optical characteristics of the glass materials 71 and 72, and the scan light 42 is diffracted by the characteristics of the diffraction elements of the diffractive surfaces 93 and 96.

The laser beam 40 emitted from the light source 10 is converted into convergence light by the lens 91, reflected by the half mirror 99, and emitted to the scan mirror 12. The scan light 42 scanned by the scan mirror 12 transmits the half mirror 99 and enters the diffractive surface 93 of the reflection unit 92. The scan light 42 which has entered the diffractive surface 93 is refracted by a diffractive function of the diffractive surface 93 and emitted to the free curved surface mirror 94. The scan light 42 reflected by the free curved surface mirror 94 returns to the diffractive surface 93, is further refracted by the diffractive surface 93, and is emitted from the reflection unit 92. The scan light 42 is converged at the convergence point 60 by the positive light condensing power of the free curved surface mirror 94, and then emitted to the projection unit 95. The lens 98 is disposed at the convergence point 60. The laser beam 40 constituting the scan light 42 enters the diffractive surface 96 of the projection unit 95 as the diffusion light by the lens 98. Thus, the reflection unit 92 is an example of a second light converging unit that converges the scan light 42 at the convergence point 60 in front of the projection unit 95, and then irradiates the projection unit 95 with the scan light 42.

The scan light 42 which has entered the projection unit 95 is refracted by the diffractive function of the diffractive surface 96 and emitted to the free curved surface mirror 97. The scan light 42 reflected by the free curved surface mirror 97 returns to the diffractive surface 96, is further refracted by the diffractive surface 96, and emits from the projection unit 95. The scan light 42 emitted from the projection unit 95 is converged at the convergence point 62 in the vicinity of the pupil 54 by the positive light condensing power of the free curved surface mirror 97, and then is emitted to the retina 52. Thus, the projection unit 95 is an example of a first light converging unit that converges the scan light 42 at the convergence point 62 in the vicinity of the pupil 54, and then irradiates the retina 52 with the scan light 42.

As with the projection optical system 20 of the first embodiment, in the scan light 42 of the projection optical system 90, the scan mirror 12 and the convergence point 60 are in the conjugate relationship with the same magnification through the reflection unit 92, and the convergence point 60 and the convergence point 62 are in the conjugate relationship with the same magnification through the projection unit 95. Therefore, in the scan light 42, the scan mirror 12 and the convergence point 62 are in the conjugate relationship with the same magnification through the reflection unit 92 and the projection unit 95.

In the first embodiment, the case where the projection optical system 20 including the reflection mirror 22 and the projection mirror 24 is provided has been described as an example, but the embodiment is not limited to this case. As in the third embodiment, the projection optical system 90 which has the reflection unit 92 including the glass material 71, the diffractive surface 93 and the free curved surface mirror 94, and the projection unit 95 including the glass material 72, the diffractive surface 96 and the free curved surface mirror 97 may be provided. The reflection unit 92 and the projection unit 95 refract and diffract the scan light 42 at the positions of the diffractive surfaces 93 and 96, and reflect the scan light 42 with the free curved surface mirrors 94 and 97. Even in this case, as in the first embodiment, it is possible to project the good-quality image in which the distortions and the like are suppressed.

When a color image is projected on the retina 52, a light source unit including three types of light sources (for example, laser diode chips) having different wavelengths of R, G and B is used as the light source 10. When the laser beams having different wavelengths are refracted by an optical element such as the same lens, the refractive indexes differ depending on the wavelengths, so that the three types of laser beams are not condensed at the same point, astigmatism might occur, and a so-called ghost might occur. Since the reflection unit 92 and the projection unit 95 have the glass materials 71 and 72, when the color image is projected using the light source unit including the three types of light sources having different wavelengths of R, G and B as the light source 10, the ghost due to the astigmatism might occur. Therefore, in the third embodiment, the reflection unit 92 and the projection unit 95 are configured to include the diffractive surfaces 93 and 96. The diffractive surfaces 93 and 96 have characteristics that correct (cancel) the astigmatism due to the glass materials 71 and 72 with respect to the laser beams 40 having different wavelengths of R, G and B. Thereby, the astigmatism of the laser beams 40 of R, G and B that enter and are reflected from the reflection unit 92 and the projection unit 95 is reduced, and the ghost of the projected color image is reduced.

As shown in FIG. 10, the lens 98 for making the laser beam 40 enter the projection unit 95 as the diffusion light is provided at the convergence point 60. The lens 98 has an optical characteristic which converts the laser beam 40 into the convergence light, and the laser beam 40 is condensed in front of the projection unit 95 by the lens 98 and then becomes the diffusion light to enter the projection unit 95. The laser beam 40 is made to enter the projection unit 95 as the diffusion light, so that the laser beam 40 is emitted to the eye 50 as the substantially collimated light by the positive light condensing power of the free curved surface mirror 97 of the projection unit 95. Thereby, as described in the second embodiment, the good-quality image in which defocusing is suppressed can be projected.

As shown in FIG. 10, the lens 91 for making the laser beam 40 enter the reflection unit 92 as the diffusion light is provided. The lens 91 has an optical characteristic which converts the laser beam 40 into the convergence light, and the laser beam 40 is condensed in front of the reflection unit 92 by the lens 91 and then becomes the diffusion light to enter the reflection unit 92. Thereby, the laser beam 40 in which the diffusion level is suppressed by the positive light condensing power of the free curved surface mirror 94 of the reflection unit 92 can be made to enter the lens 98, as described in the second embodiment. Therefore, a lens having a special specification need not to be used as the lens 98 which makes the laser beam 40 enter the projection unit 95 as the appropriate diffusion light.

When the image projection device 300 according to the third embodiment is applied to a head-mounted display, an installation space of the projection optical system 90 is limited. Therefore, it is preferable that the reflection unit 92 and the projection unit 95 refract the laser beam 40 with a certain degree of refraction angle and condense the laser beam 40 with a certain degree of light condensing power. The reflection unit 92 and the projection unit 95 include optimized glass materials 71 and 72, optimized diffractive surfaces 93 and 96, and optimized free curved surface mirrors 94 and 97, respectively, so that an optimum refraction angle and an optimum light condensing power as the head-mounted display can be obtained. With this configuration, the diffractive power of the diffractive surfaces 93 and % can be made as small as possible, so that it is not necessary to reduce a pitch of the diffractive element. Therefore, a diffraction accuracy thereof is increased and the manufacture is further facilitated.

The astigmatism may occur also when the laser beams 40 having different wavelengths of R, G and B transmit the lenses 91 and 98. In order to avoid this, the astigmatism can be reduced (cancelled) by installing diffraction elements on the surfaces of the lenses 91 and 98.

The reflection unit 92 is not configured symmetrically with respect to the horizontal and vertical scan directions of the scan mirror 12 in order to guide the laser beam 40 from the light source 10 to the eye 50. Therefore, the light condensing powers in the horizontal direction and the vertical direction are made different by forming the lens 91 in a semi-cylindrical shape or the like, which makes it possible to correct (cancel) the astigmatism due to asymmetry in the horizontal and vertical directions of the reflection unit 92.

The laser beam 40 converted into the convergence light by the lens 91 is reflected by the half mirror 99 and emitted to the scan mirror 12. Thereby, the structure in which the laser beam 40 is emitted to the scan mirror 12 from the front can be realized, and the distortion of the projection image can be reduced as with the first variation of the second embodiment. Here, the laser beam 40 emitted from the light source 10 may be directly emitted to the scan mirror 12 after passing through the lens 91 without via the half mirror 99.

In the configurations of the first and second embodiments, the laser beam is converged with the positive light condensing powers of the reflection mirror 22 and the projection mirror 24. Therefore, the distances from the mirrors to the convergence points are reduced by increasing the light condensing powers. Thereby, it is possible to realize the downsizing of the image projection device. To this end, however, the curvatures of the free curved surface mirrors of the reflection mirror 22 and the projection mirror 24 are increased, which may be an obstacle to the downsizing of the image projection device in this case. On the other hand, as in the third embodiment, the reflection unit 92 and the projection unit 95 include the diffractive surfaces 93 and 96, so that the laser beam 40 is refracted by the diffractive surfaces 93 and %. Therefore, the curvatures of the free curved surface mirrors 94 and 97 can be reduced. In this case, although they are the free curved surfaces, they can be made close to flat mirrors as much as possible, so that further downsizing of the image projection device can be realized.

According to the third embodiment, the ratio of the optical path length in which the laser beam 40 travels from the free curved surface mirror 94, is diffracted by the diffractive surface 93 and travels to the convergence point 60 to the optical path length in which the laser beam 40 travels from the scan mirror 12, is diffracted by the diffractive surface 93 and travels to the free curved surface mirror 94 is substantially the same size as the ratio of the optical path length in which the laser beam 40 travels from the convergence point 60, is diffracted by the diffractive surface 96 and travels to the free curved surface mirror 97 to the optical path length in which the laser beam 40 travels from the free curved surface mirror 97, is diffracted by the diffractive surface 96 and travels to the convergence point 62. Thereby, also in the third embodiment, the influence of the positive light condensing power of the free curved surface mirror 97 on the laser beam 40 can be canceled by the influence of the positive light condensing power of the free curved surface mirror 94 on the laser beam 40, in the same manner as described in FIG. 4A of the first embodiment. Therefore, it is possible to project the good-quality image in which the distortions and the like are suppressed.

In FIG. 10, the reflection unit 92 and the projection unit 95 are thickened for the sake of explanation. However, in practice, the reflection unit 92 and the projection unit 95 can be thinned in accordance with a minimum optical path length, and the thickness can be about 2.5 mm at the center thereof, so that they can be embedded in the eyeglass lens.

In the first to third embodiments, the case where the image is projected onto one eye 50 has been described as an example, but the image may be projected onto both eyes 50. Moreover, the scan mirror 12 has been described as an example scan unit, but the scan unit may be any element as long as it can scan a light beam. For example, other components such as potassium tantalate niobate (KTN) crystal that is an electro-optic material may be used as the scan unit. The case where the light beam is a laser beam has been described as an example, but the light beam may be light other than the laser beam.

Figure 11:
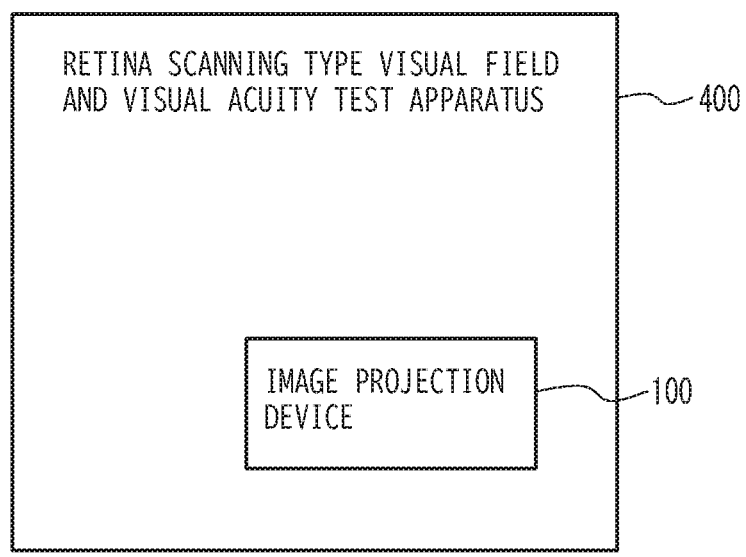
FIG. 11 is a block diagram showing a retina scanning type visual field and visual acuity test apparatus.

FIG. 11 is a block diagram showing a retina scanning type visual field and visual acuity test apparatus. As shown in FIG. 11, a retina scanning type visual field and visual acuity test apparatus 400 includes the image projection device 100 of the first embodiment. The image projection device of the second embodiment, the first variation of the second embodiment or the third embodiment may be provided instead of the image projection device 100 of the first embodiment. For example, if the configurations disclosed in the first to third embodiments are applied to the retina scanning type visual field and visual acuity test apparatus and a retina scanning type head-mounted display disclosed in Japanese Patent Application Publications Nos. 2017-106337 and 2017-111151, the configurations can be used to project an image and an index on the retina scanning type head-mounted display based on visual characteristic data of the user inspected by the retinal scanning visual acuity inspection device.

Although embodiments of the present invention have been specifically described, the present invention is not limited to those particular embodiments, and various changes and modifications may be made to them without departing from the scope of the invention disclosed in the claims.

DESCRIPTION OF REFERENCE NUMERALS 10 light source
11 emission surface
12 scan mirror
13 scan surface
14 lens
projection optical system
22 reflection mirror
24 projection mirror
26 lens
30 control unit
32 image input unit
40, 40a laser beam
42 scan light
50 eye
52 retina
54 pupil
56 crystalline lens
58 cornea
60, 62 convergence point
71, 72 glass material
82 reflection mirror
84 lens
86 reflection half mirror
90 projection optical system
91, 98 lens
92 reflection unit
93, 96 diffractive surface
94, 97 free curved surface mirror
95 projection unit
99 half mirror
100-300, 500, 600 image projection device
400 retina scanning type visual field and visual acuity test apparatus

The invention claimed is:

1. An image projection device that project an image onto a user's retina, comprising:
   a light source that emits a laser beam;
   a control unit that generates an image light beam based on input image data, and controls emission of the image light beam from the light source;
   a scan unit that scans the image light beam emitted from the light source to convert the image light beam into scan light;
   a first light converging unit that is disposed in front of a user's eye, converges the scan light at a first convergence point in the vicinity of a pupil of the user's eye, and then irradiates the retina with the scan light to project the image on the retina; and
   a second light converging unit and that converges the scan light scanned by the scan unit at a second convergence point in front of the first light converging unit, and then irradiates the first light converging unit with the scan light;
   wherein a scan angle of the scan light by the scan unit is substantially the same size as a convergence angle at which the scan light converges to the first convergence point, and
   wherein a focal length of the second light converging unit is shorter than that of the first light converging unit.

2. The image projection device according to claim 1, wherein
   in the image light beam, a ratio of an optical path length between the second light converging unit and the second convergence point to an optical path length between the scan unit and the second light converging unit is substantially the same size as a ratio of an optical path length between the second convergence point and the first light converging unit to an optical path length between the first light converging unit and the first convergence point.

3. The image projection device according to claim 1, wherein
   the first light converging unit and the second light converging unit are minors that reflect the scan light, and
   in the image light beam, a bending angle at the first light converging unit s substantially the same size as a bending angle at the second light converging unit.

4. An image projection device that project an image onto a user's retina, comprising:
   a light source that emits a laser beam;
   a control unit that generates an image light beam based on input image data, and controls emission of the image light beam from the light source;
   a scan unit that scans the image light beam emitted from the light source to convert the image light beam into scan light;
   a first light converging unit that is disposed in front of a user's eye, converges the scan light at a first convergence point in the vicinity of a pupil of the user's eye, and then irradiates the retina with the scan light to project the image on the retina;

a second light converging unit that converges the scan light scanned by the scan unit at a second convergence point in front of the first light converging unit, and then irradiates the first light converging unit with the scan light; and a first optical member that is provided at the second convergence point and makes the image light beam enter the first light converging unit as diffusion light, wherein the first optical member has an optical characteristic which converts the image light beam into convergence light, and wherein the image light beam is condensed in front of the first light converging unit by the first optical member, and then becomes the diffusion light to enter the first light converging unit.

5. The image projection device according to claim 4, wherein in the image light beam, a ratio of an optical path length between the second light converging unit and the second convergence point to an optical path length between the scan unit and the second light converging unit is substantially the same size as a ratio of an optical path length between the second convergence point and the first light converging unit to an optical path length between the first light converging unit and the first convergence point.

6. The image projection device according to claim 4, comprising a second optical member for making the image light beam enter the second light converging unit as the diffusion light.

7. The image projection device according to claim 6, wherein the second optical member has an optical characteristic which converts the image light beam into the convergence light, and the image light beam is condensed in front of the second light converging unit by the second optical member, and then becomes the diffusion light to enter the second light converging unit.

8. The image projection device according to claim 6, wherein the second optical member is provided on an optical path of the image light beam between the light source and the scan unit, and makes the image light beam enter the scan unit as the convergence light, and the image light beam is emitted from the scan unit as the convergence light, condensed in front of the second light converging unit, and then becomes the diffusion light to enter the second light converging unit, is emitted from the second light converging unit as the diffusion light, is condensed in front of the first light converging unit by the first optical member, and then becomes the diffusion light to enter the first light converging unit, and is emitted from the first light converging unit as substantially collimated light.

9. The image projection device according to claim 1, wherein the light source is disposed at a position facing the scan unit, the second light converging unit includes a half mirror, and the half mirror transmits the laser beam emitted from the light source.

10. An image projection device that project an image onto a user's retina, comprising:

a light source that emits a laser beam;

a control unit that generates an image light beam based on input image data, and controls emission of the image light beam from the light source;

a scan unit that scans the image light beam emitted from the light source to convert the image light beam into scan light;

a first light converging unit that is disposed in front of a user's eye, converges the scan light at a first convergence point in the vicinity of a pupil of the user's eye, and then irradiates the retina with the scan light to project the image on the retina; and a second light converging unit that converges the scan light scanned by the scan unit at a second convergence point in front of the first light converging unit, and then irradiates the first light converging unit with the scan light;

wherein each of the first light converging unit and the second light converging unit includes a glass material, a diffractive surface, and a curved surface mirror, and the scan light is refracted and diffracted at a position of the diffractive surface, and reflected by the curved mirror.

11. The image projection device according to claim 10, wherein the light source emits a plurality of laser beams having different wavelengths, and astigmatism due to a refraction characteristic of the glass material in the first light converging unit or the second light converging unit is corrected by a diffraction characteristic of the diffractive surface.

12. The image projection device according to claim 10, comprising:

a third optical member for making the image light beam enter the first light converging unit as diffusion light that is provided at the second convergence point;

wherein the third optical member has an optical characteristic which converts the image light beam into convergence light, and the image light beam is condensed in front of the first light converging unit by the third optical member, and then becomes the diffusion light to enter the first light converging unit.

13. The image projection device according to claim 12, wherein the third optical member has a diffractive surface on a surface thereof.

14. The image projection device according to claim 10, comprising:

a fourth optical member for making the image light beam enter the second light converging unit as the diffusion light;

wherein the fourth optical member has an optical characteristic which converts the image light beam into the convergence light, and the image light beam is condensed in front of the second light converging unit by the fourth optical member, and then becomes the diffusion light to enter the second light converging unit.

15. The image projection device according to claim 14, wherein the fourth optical member has a diffractive surface on a surface thereof.

16. The image projection device according to claim 10, wherein in the image light beam, a ratio of an optical path length between the second light converging unit and the second convergence point to an optical path length between the scan unit and the second light converging unit is substantially the same size as a ratio of an optical path length between the second convergence point and the first light converging unit to an optical path length between the first light converging unit and the first convergence point.

17. A retina scanning type visual field and visual acuity test apparatus, comprising:
the image projection device according to claim 10.

\* \* \* \* \*